United States Patent
Vick

(10) Patent No.: US 6,699,090 B1
(45) Date of Patent: Mar. 2, 2004

(54) SOFT TOYS WITH CHARACTERISTIC INDICIES

(76) Inventor: T. Kevin Vick, 113 Pony Ct., Thomasville, GA (US) 31792

( * ) Notice: Subject to any disclaimer, the term of this patent is extended or adjusted under 35 U.S.C. 154(b) by 0 days.

(21) Appl. No.: 10/205,034

(22) Filed: Jul. 24, 2002

Related U.S. Application Data

(63) Continuation-in-part of application No. 09/971,356, filed on Oct. 4, 2001.

(51) Int. Cl.[7] .............................. A63H 3/00; A63H 3/02
(52) U.S. Cl. ......................................... 446/73; 446/369
(58) Field of Search ................................ 446/369, 385, 446/71, 72, 73, 75, 76, 77

(56) References Cited

U.S. PATENT DOCUMENTS

| | | | | |
|---|---|---|---|---|
| 5,037,343 A | * | 8/1991 | Benites ........................ 446/268 |
| 5,676,583 A | * | 10/1997 | Wang et al. ................. 446/268 |
| 6,299,374 B1 | * | 10/2001 | Naor et al. .................. 401/198 |
| 6,520,826 B2 | * | 2/2003 | Spector ........................ 446/73 |

* cited by examiner

Primary Examiner—Derris H. Banks
Assistant Examiner—Faye Francis
(74) Attorney, Agent, or Firm—Baker, Donelson, Bearman, Caldwell & Berkowitz

(57) ABSTRACT

A stuffed, soft body scent-emitting character (10) formed from a fabric material (12) and filled with a stuffing material to provide volumetric definition of the character with a chamber that receives scent-emittive materials sensible exterior thereof and defining a scent indicia. At least one visual indicia correlated with the scent emittive material attaches to the fabric material and is selected from a group comprising a name indicia and a coloring indicia. The character, receiving the scent emittive material in the chamber, provides a soft toy that emits the scent correlated with the visual indicia.

18 Claims, 2 Drawing Sheets

SOFT TOYS WITH CHARACTERISTIC INDICIES

The present application is a continuation-in-part of co-pending patent application Ser. No. 09/971,356 filed Oct. 4, 2001.

TECHNICAL FIELD

The present application relates to toys. More particularly, the present invention relates to soft, stuffed toys having characteristic indicies for play while emitting desirable scenting of the air.

BACKGROUND OF THE INVENTION

Stuffed, soft bodied animal and personage characters have long been a favorite toy for young children. Rarely are a group of young children seen, such as at airports, camps, and the like, where at least some of the children are carrying stuffed animals or characters. These play toys are readily huggable and have a comforting effect on the children. These toys typically are manufactured from fabric materials that is cut and attached together to define bodies with various appropriate appendages. The bodies are then filled with various stuffing materials, typically soft, but firm materials are used as well. The characters often are popularly known cartoon or other characters, as well as replicas of animals and the like.

These stuffed animal and personage characters are held, played with, and otherwise used in many different locations, but generally at the home of the owner of the toy. It is to be appreciated that these various environments have differing smells and odors. Often persons attempt to modify or control the odors, and there are a variety of devices directed to such. Further, it is believed that persons may be helped in attitude and comfort if the odors in their environment are pleasing and satisfactory rather than unpleasant or disturbing.

The scenting devices heretofore known have, while providing for the scenting of air typically in bathrooms or in heating and ventilation systems, have not been entirely successful in being incorporated with articles used by children to provide a favorable fragrance in their various environments.

Further, play articles often provide learning opportunities which extend from the particular toy to cross-related concepts. These cross-related concepts enhance the play and educational value of the toy. The enhancement occurs by the user of the toy conceptualizing from ideas and features of the toy to the cross-related concepts.

Accordingly, there is a need in the art for improved soft stuffed toys for entertaining children while providing desirable scenting and enhancing cross-related conceptualizing. It to such that the present invention is directed.

BRIEF DESCRIPTION OF THE PRESENT INVENTION

The present invention meets the need in the art for an improved toy for entertaining children while providing desirable scenting with a stuffed, soft body scent-emitting character formed from a fabric material that defines an exterior form for a body of a character and a body cavity defined thereby filled with a stuffing material to provide volumetric definition of the character. A chamber within the body cavity receives scent-emittive materials and communicates a scent sensible exterior of the body cavity, the scent-emittive materials defining a scent indicia. The exterior surface includes a color indicia correlated with the scent indicia by including at least one visual characteristic indicative of the scent. A name indicia incorporates at least one symbol indicative of the scent indicia or the coloring indicia. The figurine, receiving the scent emittive material in the chamber, provides a soft toy having correlated scent, coloring, and name indicia.

In another aspect, the present invention provides a stuffed, soft body scent-emitting character, comprising a fabric material defining an exterior form for a body of a character and a body cavity defined thereby filled with a stuffing material to provide volumetric definition of the character. A chamber having a bottom and side wall extending in a first direction therefrom is received within the body cavity. The chamber receives scent-emittive materials and communicates a scent [sensible exterior of the body cavity, which defines a scent indicia. A cap defining a plurality of openings allows communicating air and is sized for removably engaging the chamber. The area of the openings in the plate is changable, for changing the volume of scented air communicated through the openings. A visual indicia attaches to the fabric material. The visual indicia is selected from a group consisting of a name indicia and a coloring indicia and correlates with the scent of the scent emittive material. The character, receiving the scent emittive material in the chamber, provides a soft toy that emits the scent correlated with the visual indicia.

Objects, features, and advantages of the present invention will become apparent from reading the following detailed description of the invention and claims in view of the appended drawings.

DETAILED DESCRIPTION OF THE PREFERRED EMBODIMENTS

Figure 1:
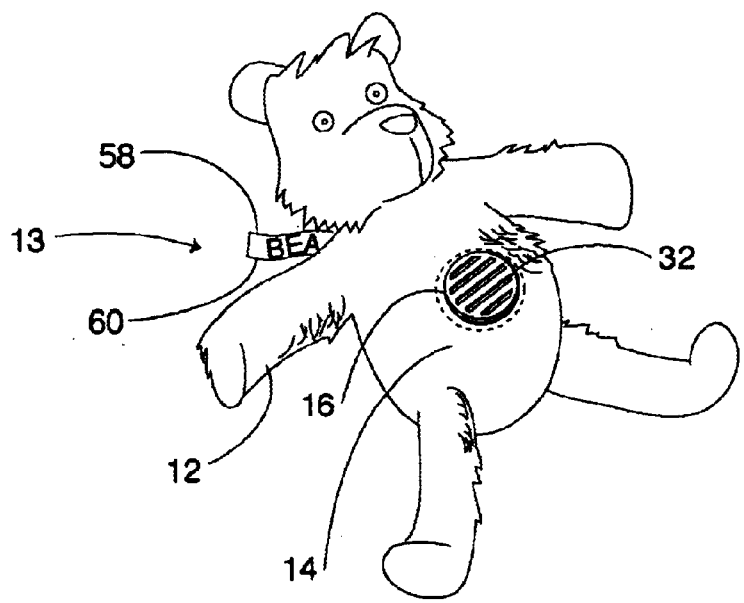
FIG. 1 illustrates in perspective view an embodiment of a stuffed, soft body scent-emitting toy according to the present invention.

Referring now in more detail to the drawings, in which like numerals indicate like parts throughout the several views, FIG. 1 is a perspective view of an embodiment of a stuffed, soft body scent-emitting toy 10 according to the present invention. The toy 10 includes a scent indicia generally 9 and at least one visual indicia of a name indicia generally 13 and a coloring indicia generally 15, which indicia 9, 13, and 15 correlate as indicative of the characteristics of the toy. The toy 10 comprises a character-ornamented figurine, and by this is meant that the toy has character attributes such as arms, legs, head, and the like associated with a character. In the illustrated embodiment, the character is a bear-like creature, but the toy can be any number of configurations based on artistic inclination. Thus, the character can take the likeness of a conventional known animal or personality, a conventional known animal or personality with artistic interpretations such as changing colorings, shapes, body features, and the like, or an imaginary character.

A fabric material generally 12 defines an exterior surface which is cut and attached together, such as by sewing, sonic welding, or the like to define a body or volumetric definition of the toy 10. The fabric material 12 incorporates the coloring indicia 15. The coloring indicia 15 denotes or relates to an object having a name or term that is related to the name indicia 13, a scent or fragrance related to the scent indicia 9, or both. The coloring indicia 15 is generally a color, a first or primary color and a plurality of secondary colors, and patterns or shading such as skin texturing (for example, an alligator). The coloring indicia 15 is perceived visually. Upon perception, the coloring indicia brings into thought of the user of the toy 10 the correlated name indicia 13 and the scent indicia 9. The body defines an internal cavity which is filled with a conventional stuffing material 11 (see FIG. 2) to define volumetric dimensions of the body of the toy 10. A portion 14 of the fabric material 12 defines an opening which receives a chamber 16.

Figure 2:
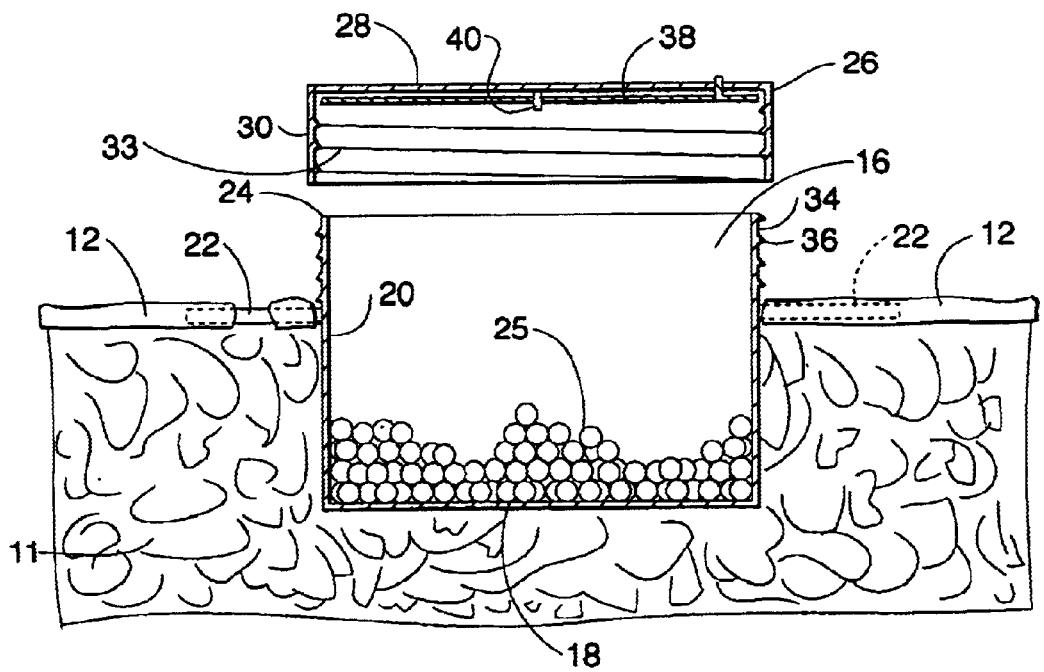
FIG. 2 is a side cross-sectional view taken along line 2—2 in FIG. 1, to illustrate features of the invention.

The chamber 16 is better illustrated in cross-sectional view in FIG. 2. The chamber 16 includes a bottom 18 and side wall 20 extending in a first direction. A flange 22 illustrated in partial cut-away view extends laterally about a perimeter of the chamber. The flange 22 is disposed spaced apart and remote from the bottom 18 but recessed relative to a distal edge 24 of the side wall 20. The chamber 16 receives and holds articles, such as scent materials 25 that comprise the scent indicia 9. The scent indicia 9 denotes or relates to an object having a scent or fragrance that is related to the name indicia 13, to the coloring indicia 15, or to both. The scent indicia 9 is perceived by smelling (ofactorily), which upon perception, brings into thought of the user of the toy 10 the correlated name indicia 13 and the coloring indicia 15. The scent materials 25 can be a plurality of conventional scent beads, provided to the chamber 16 either a group of loose beads or contained within a package, or other scent material conventional in the trade.

A cap 26 includes a plate 28 and a skirt 30 that extend a predetermined distance from a perimeter edge of the plate 28. The cap 26 is sized for removably engaging the distal edge portion of the side wall 20 of the chamber 16. As best illustrated in FIG. 1, the plate 28 defines a plurality of spaced-apart openings 32 for communicating air from the chamber 16. The openings 32 are illustrated as substantially rectangular cut-outs, but other patterns can be employed, such circular (see the embodiment in FIG. 3, curvilinear (see the embodiment in FIG. 4), or other pattern. In the illustrated embodiment, the interior surface of the skirt 30 defines a thread 33.

The flange 22 and the fabric material 12 around the opening in the portion 14 connect together, whereby the chamber 16 is held in the body of the toy 10. The fabric material 12 connects to the flange 22 preferably by an adhesive, although the flange 22 can be sown to the fabric material with a cord or thread, connected with rivets, secured with sonic welding, or other similar engagement mechanism.

A distal edge portion 34 of the side wall 20 extends slightly outwardly of the body of the toy 10. The distal end portion 34 defines a thread 36 on the exterior surface. The thread 36 engages the thread 33 of the cap to secure the cap to the chamber 16.

Figure 4:
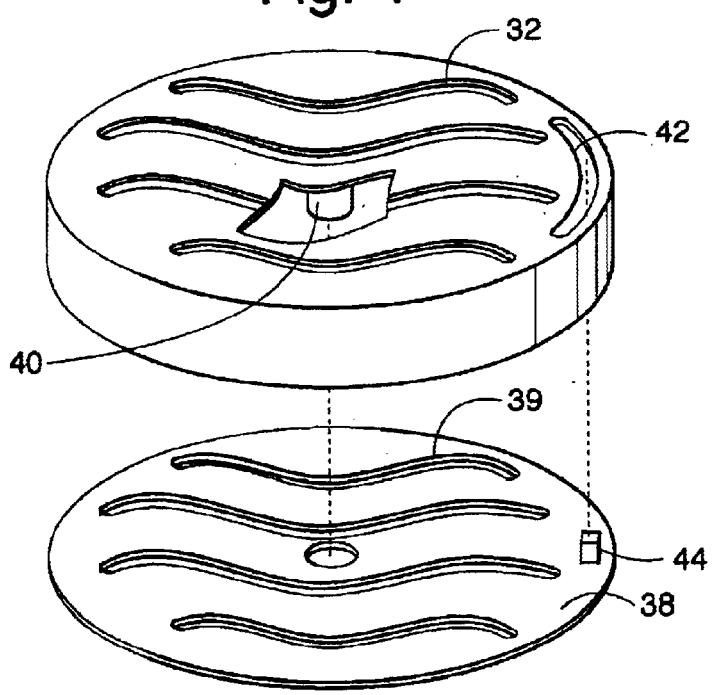
FIG. 4 is an exploded view of the cap for closing the chamber in the toy illustrated in FIG. 1.

The cap 26 includes a rotatable disk 38 that defines openings 39 (see FIG. 4) corresponding substantially to the openings 32 in the plate 28. FIG. 4 illustrates an alternate embodiment in exploded view with a different configuration of openings 32, 39 to suggest the possible variations. The disk 38 connects by a pin 40 extending from a central portion of the plate 28. The openings 39 in the disk 38 selectively register with the openings 32, so that the effective cross-sectional area of the openings through the cap can be changed to adjust the volume of air communicated through the openings.

With continued reference to FIGS. 2 and 4, the plate 38 further defines an arcuate slot 42 in a side portion. The disk 38 includes a tab 44 that projects through the arcuate slot 42. The tab 44 permits the disk 38 to be rotated between between a first position at a first end of the arcuate slot 42 and a second position at an opposing end of the arcuate slot. Stopping the tab 44 at an intermediate position brings the openings in the disk 38 into at least partial registration with the openings in the plate 28, for varying selectively the communication of air from the chamber 16.

Figure 3:
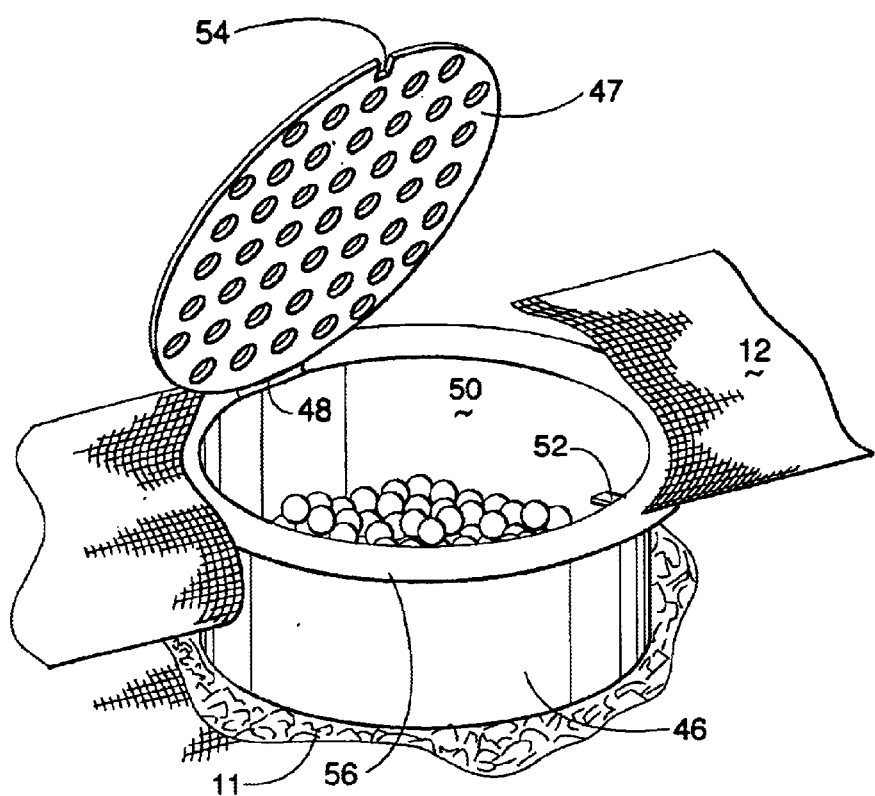
FIG. 3 is a perspective view of an alternate embodiment of a chamber received in the soft body toy illustrated in FIG. 1.

FIG. 3 is a perspective view of an alternate embodiment of a chamber 46 received in the soft body toy 10 illustrated in FIG. 1. In this embodiment, a cap 47 connects by a hinge 48 at an edge of a side wall 50 of the chamber 46. A pin 52 extends radially from an inner wall surface near the distal edge of the side wall 50. The cap 47 defines a slot 54 in the skirt in alignment with the pin 52. The cap 47 pivots closed on the hinge 48 and is secured closed by engaging the pin 52 in the slot 54 of the cap. It is to be appreciated that other fastening mechanisms can be gainfully used to hold the cap to the chamber, such as a groove and projecting ring that interlock, a flap extending laterally from the sidewall 50 which flap overlaps a side edge of the cap 47 and locks to a tab protruding from an exterior surface of the cap, and other such latching structures. In the embodiment illustrated in FIG. 3, a flange 56 extends laterally at a distal edge of the side wall 50, for engaging the chamber 46 to the fabric material 12, as discussed above.

The name indicia 13 in the illustrated embodiment comprises a tag 58 bearing printed letters 60 of the name of the toy 10. It is to be appreciated that the name indicia may also comprise symbols, names, words, numbering, or other indicators of identity of the toy. However, within the scope of the present invention, the name indicia 13 denotes or relates to an object having a color, to a scent or fragrance, or to both. The name indicia 13 is perceived visually and also audibly when the name indicia 13 is spoken. Upon perception, the name indicia 13 brings into thought the correlated scent indicia 9 and the coloring indicia 15.

The toy 10 is used as plaything, such as by children. The chamber 16 receives the scent material 25, and the cap 26 is closed. In the illustrated embodiment, the cap 26 threadingly engages the thread 36 on the side wall 20. The scent material 25 volatilizes, and scent vapors communicate through the openings 32 in the cap 26. The strength of the scent emitted by the toy 10 can be adjusted. This is accomplished by moving the tab 44 in the slot 42. To reduce the scent, the openings in the disk 38 are taken out of registration with the openings in the plate 38. This reduces the cross-sectional area of the openings, which allows a smaller volume of scent to be communicated. Conversely, to increase the effect of the scent, the openings are brought into registration to increase the cross-sectional area for communication of the scent. It is to be appreciated that other control mechanisms such as louvers, sliding covers, and the like, can be used. Upon expiration of the effectiveness of the scent material 25, the cap 26 is opened and the scent material replaced. A variety of fragrances are commercially available from fragrance suppliers to meet the various personal preferences of persons using the toy 10.

The toy 10 of the present invention accordingly provides a character having the correlated scent indicia 9, name indicia 13, and coloring indicia 15. Various illustrative embodiments are described below.

Character 1

Name indicia: HONEY BEAR

Scent indicia: Honey

Coloring indicia: Golden brown

The embodiment of character 1 having golden brown coloring indicia includes the three correlated name, scent, and coloring indicias. An embodiment of a different color or color pattern would have only the two correlated indicia.

Character 2

Name indicia: PEPPERMINT PANDA soft toy

Scent indicia: peppermint

Coloring indicia: red and white

The embodiment of character 2 having red and white coloring indicia includes the three correlated name, scent, and coloring indicias while an embodiment of a different color or color pattern would have only the two correlated indicia.

Character 3

Name indicia: WATERMELON WALUS soft toy

Scent indicia: watermelon

Coloring indicia: red

The embodiment of character 3 having red coloring indicia includes the three correlated name, scent, and coloring indicias while an embodiment of a different color or color pattern would have only the two correlated indicia.

Character 4

Name indicia: CHOCO RABBIT soft toy

Scent indicia: chocolate

Coloring indicia: brown

The embodiment of character 4 having brown coloring indicia includes the three correlated name, scent, and coloring indicias while an embodiment of a different color would have only the two correlated indicia.

Character 5

Name indicia: ORANGE PENGUIN soft toy

Scent indicia: orange

This embodiment of character 5 includes the correlated scent indicia and name indicia. In an embodiment of character 5 having orange coloring, the color indicia would be correlated.

Character 6

Name indicia: LEMON LION soft toy

Scent indicia: lemon

Coloring indicia: yellow

The embodiment of character 6 having yellow coloring indicia includes the three correlated name, scent, and coloring indicias while an embodiment of a different color or color pattern would have only the two correlated indicia.

The present invention accordingly provides the stuffed, soft body scent-emitting toy having correlated scent, name, and/or coloring indicia suitable for comfort and play while selectively scenting the air and enhancing cross-relational conceptualizing by the user of the toy. The principles, preferred embodiments, and modes of operation of the present invention have been described in the foregoing specification. The invention is not to be construed as limited to the particular forms disclosed because these are regarded as illustrative rather than restrictive. Moreover, variations and changes may be made by those skilled in the art without departure from the spirit of the invention as described by the following claims.

What is claimed is:

1. A stuffed, soft body scent-emitting toy, comprising:

a character-ornamented figurine defined by an exterior surface of a fabric material and having an internal cavity filled with a stuffing material to define a body thereof;

a chamber within the body which receives scent-emittive materials and communicating a scent therefrom which is sensible exterior of the body, the scent-emittive materials defining a scent indicia;

a coloring indicia on the exterior surface and correlated with the scent indicia by including at least one visual characteristic indicative of the scent; and a name indicia incorporating at least one symbol indicative of the scent indicia or the coloring indicia, whereby the figurine, receiving the scent emittive material in the chamber, provides a soft toy having correlated scent, coloring, and name indicia.

2. The stuffed, soft body scent-emitting toy as recited in claim 1, wherein the name indicia comprises a tag attached to the body and bearing the symbol interpretable as an identifier of the figurine.

3. The stuffed, soft body scent-emitting toy as recited in claim 2, wherein the symbol comprises letters spelling the name of the figurine.

4. The stuffed, soft body scent-emitting toy as recited in claim 1, wherein the chamber has a bottom and a side wall extending in a first direction therefrom and received in an opening of the figurine;

and further comprising:

a cap sized for removably engaging the chamber and defining a plurality of spaced-apart openings for communicating air therethrough.

5. A stuffed, soft body scent-emitting character, comprising:

a fabric material defining an exterior form for a body of a character and a body cavity defined thereby filled with a stuffing material to provide volumetric definition of the character;

a chamber within the body cavity which receives scent-emittive materials and communicating a scent sensible exterior of the body cavity, the scent-emittive materials defining a scent indicia;

a coloring indicia on the exterior surface and correlated with the scent indicia by including visual characteristics that are indicative of the scent; and a name indicia incorporating a text word indicative of the scent or the coloring, whereby the character, receiving the scent emittive material in the chamber, provides a soft toy that emits the scent suggested by the coloring and name indicia.

6. The stuffed, soft body scent-emitting toy as recited in claim 5, wherein the name indicia comprises a tag attached to the body and bearing the text word interpretable as an identifier of the character.

7. The stuffed, soft body scent-emitting toy, as recited in claim 5, wherein the chamber comprises:
- a bottom and a side wall extending in a first direction therefrom and received in an opening of the fabric material;
- a cap defining a plurality of openings therein for communicating air therethrough and sized for removably engaging the chamber; and
- means for changing the cross-sectional area of the openings in the plate, for changing the volume of scented air communicated through the openings.

8. The stuffed, soft body scent-emitting toy, as recited in claim 7, wherein the cap comprises:
- a plate that defines the plurality of openings, the plate further defining an arcuate slot in a side portion;
- a pin extending from the plate; and
- a disk having a plurality of openings which are conformable with the openings in the plate, the disk rotatably mounted to the plate by the pin and a tab projecting from a side portion of the disk for alignment with the arcuate slot in the plate,
- whereby the disk, being rotated by the tab moving in the slot, selectively aligns the openings in the disk with the openings in the plate for selectively changing the communication of scent from the chamber.

9. A stuffed, soft body scent-emitting character, comprising:
- a fabric material defining an exterior form for a body of a character and a body cavity defined thereby filled with a stuffing material to provide volumetric definition of the character;
- a chamber having a bottom and side wall extending in a first direction therefrom received within the body cavity, which receives scent-emittive materials and communicating a scent sensible exterior of the body cavity, the scent-emittive materials defining a scent indicia;
- a cap defining a plurality of openings therein for communicating air therethrough and sized for removably engaging the chamber;
- means for changing the cross-sectional area of the openings in the plate, for changing the volume of scented air communicated through the openings;
- a visual indicia attached to the fabric material, the visual indicia suggesting the scent of the scent emittive material selected from a group consisting of a name indicia and a coloring indicia,
- whereby the character, receiving the scent emittive material in the chamber, provides a soft toy that emits the scent correlated with the visual indicia.

10. The stuffed, soft body scent-emitting toy as recited in claim 9, wherein the name indicia comprises a tag attached to the body and bearing symbols interpretable as an identifier of the character.

11. The stuffed, soft body scent-emitting toy as recited in claim 10, wherein the symbols are letters spelling the name of the character.

12. The stuffed, soft body scent-emitting toy as recited in claim 9, wherein the coloring indicia comprises a color correlated to the scent indicia.

13. The stuffed, soft body scent-emitting toy as recited in claim 9, wherein the visual indicia includes coloring affixed to the fabric material.

14. The stuffed, soft body scent-emitting toy as recited in claim 9, wherein the visual indicia suggests an object that emits a fragrance similar to the scent.

15. The stuffed, soft body scent-emitting toy as recited in claim 9, wherein the visual indicia suggests an object having a name correlated to the scent.

16. The stuffed, soft body scent-emitting toy as recited in claim 9, wherein the visual indicia suggests an object that emits a fragrance similar to the scent.

17. The stuffed, soft body scent-emitting toy, as recited in claim 9, wherein the chamber further comprises a flange extending laterally about a perimeter thereof, the flange disposed remote from the bottom and spaced from a distal edge of the side wall; and
- means for securing the flange to the fabric material near the opening in the fabric material.

18. The stuffed, soft body scent-emitting toy, as recited in claim 9, wherein the cap comprises:
- a plate that defines the plurality of openings, the plate further defining an arcuate slot in a side portion;
- a pin extending from a central portion of the plate; and
- a disk having a plurality of openings which are conformable with the openings in the plate, the disk rotatably mounted to the plate by the pin and a tab projecting from a side portion of the disk for alignment with the arcuate slot in the plate,
- whereby the disk, being rotated by the tab moving in the slot, selectively aligns the openings in the disk with the openings in the plate for selectively changing the communication of scent from the chamber.

\* \* \* \* \*